United States Patent
Spahn

(10) Patent No.: US 7,473,902 B2
(45) Date of Patent: Jan. 6, 2009

(54) DIGITAL RADIOGRAPHIC UNIT AND A METHOD FOR TAKING RADIOGRAPHS IN A DIGITAL RADIOGRAPHIC UNIT

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 77 days.

(21) Appl. No.: 11/244,143

(22) Filed: Oct. 6, 2005

(65) Prior Publication Data

US 2006/0086913 A1 Apr. 27, 2006

(30) Foreign Application Priority Data

Oct. 7, 2004 (DE) .................. 10 2004 048 962

(51) Int. Cl.
*G01T 1/24* (2006.01)
*G01T 1/20* (2006.01)
(52) U.S. Cl. .................. 250/370.09; 250/370.06; 250/370.11
(58) Field of Classification Search .......... 250/580, 250/370.11, 370.06, 370.09
See application file for complete search history.

(56) References Cited

U.S. PATENT DOCUMENTS

| | | | |
|---|---|---|---|
| 5,381,013 A | * | 1/1995 | Cox et al. ............... 250/370.09 |
| 5,825,033 A | * | 10/1998 | Barrett et al. ............. 250/370.1 |
| 6,175,611 B1 | * | 1/2001 | Melen et al. .................. 378/19 |
| 6,559,453 B2 | * | 5/2003 | Lundqvist .................. 250/371 |
| 7,214,944 B2 | * | 5/2007 | Rostaing et al. ........ 250/370.06 |
| 2002/0117626 A1 | * | 8/2002 | Danielsson ............ 250/370.01 |
| 2003/0223532 A1 | * | 12/2003 | Clinthorne et al. ............ 378/19 |
| 2004/0252910 A1 | * | 12/2004 | Dixon et al. ................ 382/274 |
| 2007/0114424 A1 | * | 5/2007 | Danielsson et al. .... 250/370.09 |

FOREIGN PATENT DOCUMENTS

EP 12 58 740 A2 11/2002
WO WO 2004/0490001 A1 6/2004

OTHER PUBLICATIONS

Flachbilddetektoren in der Rötgendiagnostil (M. Spahn, V. Heer, R. Freytag) Zeitschrift Radiologie 43, 2004, p. 340 to 350.

* cited by examiner

*Primary Examiner*—David P Porta
*Assistant Examiner*—Casey Bryant
(74) *Attorney, Agent, or Firm*—Harness, Dickey's Pierce, P.L.C.

(57) ABSTRACT

A digital radiographic unit is disclosed which includes a counting flat image detector for taking radiographs from an x-radiation with the aid of pixel readout units, adjacent in a matrix, for measuring and counting charge pulses generated by x-ray quanta of the x-radiation. A coincidence, occurring within a specific time interval, of charge pulses of a pixel readout unit and of charge pulses of at least one bordering pixel readout unit, is detected and the corresponding charge pulses are summed to form a total charge pulse as basic variables for a further evaluation.

11 Claims, 5 Drawing Sheets

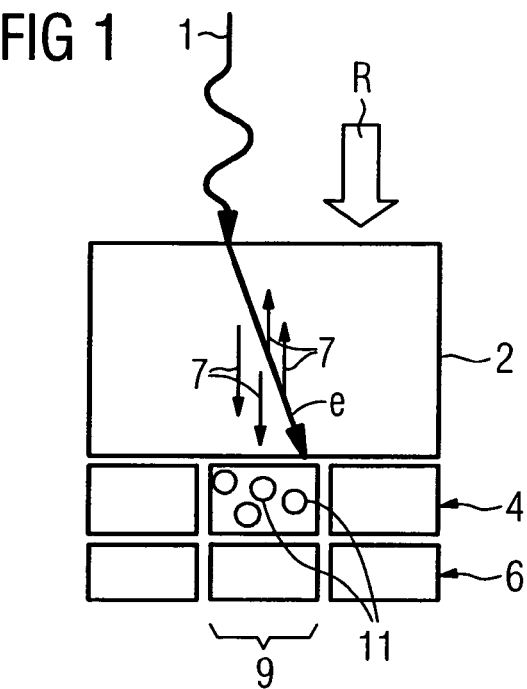
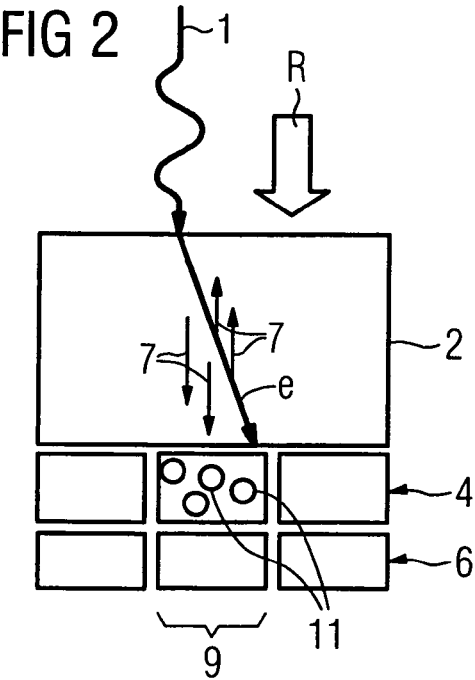
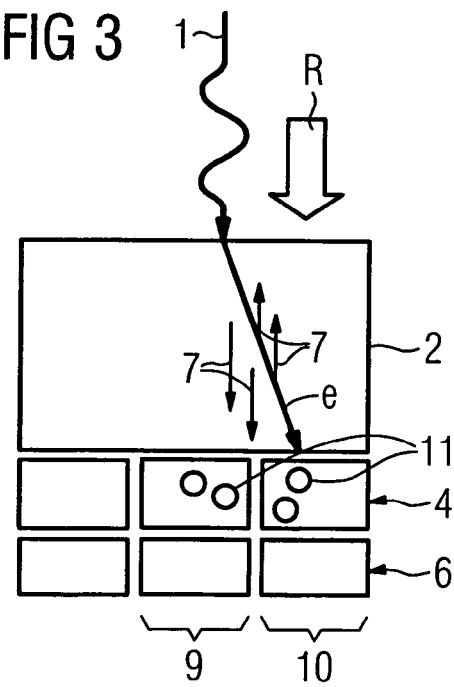
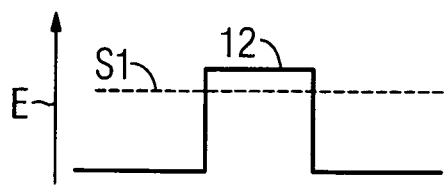
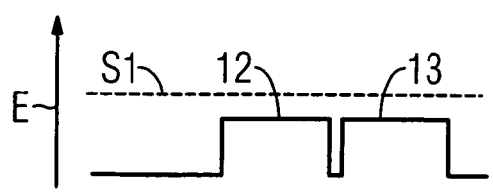

FIG 4
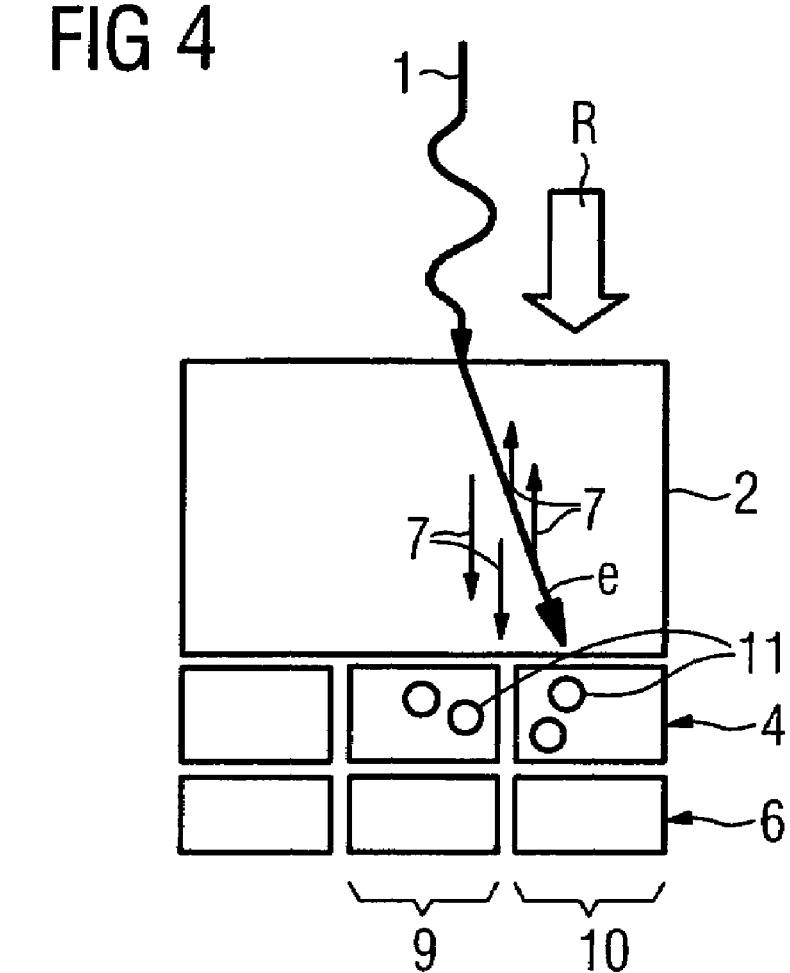
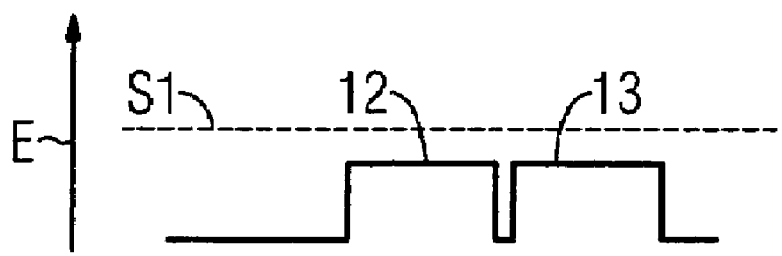
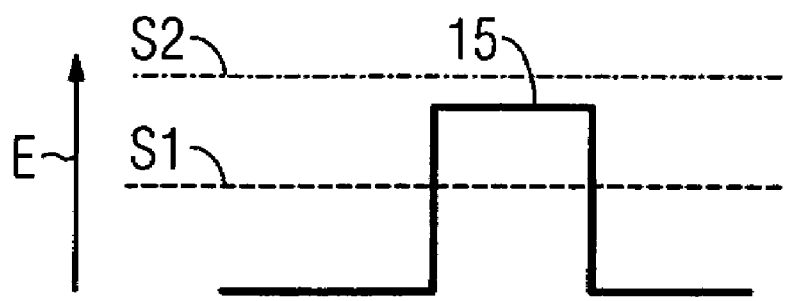

DIGITAL RADIOGRAPHIC UNIT AND A METHOD FOR TAKING RADIOGRAPHS IN A DIGITAL RADIOGRAPHIC UNIT

The present application hereby claims priority under 35 U.S.C. §119 on German patent application number DE 10 2004 048 962.9 filed Oct. 7, 2004, the entire contents of which is hereby incorporated herein by reference.

FIELD

The invention generally relates to a digital radiographic unit, and/or to a method for taking radiographs in a digital radiographic unit.

BACKGROUND

A digital radiographic unit and/or a method for taking radiographs in a digital radiographic unit are known, for example, from the article entitled "Flachbilddetektoren in der Röntgendiagnostik" ["Flat image detectors in x-ray diagnostics"] by M. Spahn, V. Heer, R. Freytag, published in the journal Radiologe 43, 2004, pages 340 to 350.

Known in x-ray imaging for the purpose of taking digital radiographs of an object are so-called flat image detectors in which an x-radiation is converted directly or indirectly into an electric charge and subsequently read out electronically by use of so-called active reader matrices and further processed for imaging.

During direct conversion, upon impinging on a direct converter layer, for example made from amorphous selenium, an x-ray quantum of the x-radiation produces a high-energy electron that in turn then generates charge carriers on its way through a direct converter layer. The charge carriers are transported with the aid of an electric field to an electrode divided into pixels, and stored there as a charge; during indirect conversion, upon impinging on a scintillator layer an x-ray quantum of the x-radiation produces a high-energy electron that in turn then generates light on its way through a scintillator layer. The light is converted into an electric charge on a photodiode, arranged below the scintillator layer and divided into pixels, and likewise stored. Subsequently, the corresponding charge pulse, which depends chiefly on the energy of the primary x-ray quantum, is read out via active switching elements assigned to electrode pixels or photodiode pixels in pixel readout units.

A distinction is made between a counting flat image detector and an integrating one. In the case of a counting detector, a charge pulse is judged to be a single x-ray quantum in a pixel readout unit, whereas in the case of an integrating detector integration is carried out over all charge pulses in a pixel readout unit. In order, in the case of a counting detector, to be able to distinguish background noise from a charge pulse originating from an x-ray quantum actually present, there is defined in general a lower threshold value above which a charge pulse is interpreted as a signal of an x-ray quantum.

SUMMARY

An object of at least one embodiment of the present invention is to achieve a largely undistorted digital radiograph of very high image sharpness in the case of a counting flat image detector.

According to at least one embodiment of the invention, an object may be achieved by a digital radiographic unit and/or by a method for taking radiographs in a digital radiographic unit.

With a digital radiographic unit and/or a method for taking radiographs of at least one embodiment of the invention, by detecting a coincidence, occurring within a specific time interval, of charge pulses of adjacent pixel readout units and summing the corresponding charge pulses to form a total charge pulse with the corresponding signal level and using the latter as a basic variable for the further evaluation, it is possible to obtain digital radiographs with greatly reduced errors. The greatly reduced errors are due to the fact that instances of multiple countings or omissions of individual x-ray quanta, whose generated charges are distributed between two or more pixel readout units and thereby distort the radiographs, are avoided. An improved radiograph of at least one embodiment is of particular importance chiefly in the case of a low x-ray dose or in detector regions on which the x-radiation does not impinge perpendicularly, since in these cases the risk of distortions is particularly high.

In a particularly simple evaluation of at least one embodiment of an improved radiograph, given a coincidence an x-radiation with one x-ray quantum and having an energy corresponding to the total charge pulse is taken as basis. It is thereby excluded that an x-ray quantum distributed over a number of pixel readout units is not counted at all or is counted several times. In order when continuing this evaluation on the one hand to avoid counting noise coincident on a number of pixel readout units as a charge pulse of an x-ray quantum, given a coincidence and an undershooting of a lower threshold value, defining a background noise, of the total charge pulse, no x-ray quantum is advantageously taken as basis. In order nevertheless, on the other hand, not to judge a simultaneous occurrence of two x-ray quanta wrongly to be a single x-ray quantum, given a coincidence and an overshooting of an upper defined threshold value of the total charge pulse an x-radiation with two x-ray quanta is expediently taken as basis.

According to a refinement of at least one embodiment of the invention, the respective time interval may be functionally dependent in terms of initiation on a pixel readout unit, in particular a central pixel readout unit, that records a first charge pulse.

BRIEF DESCRIPTION OF THE DRAWINGS

The invention and further advantageous refinements in accordance with further features are explained in more detail below in the drawings with the aid of schematically illustrated example embodiments, without thereby limiting the invention to these example embodiments; in the drawings:

FIG. 1 shows a known digital radiographic unit having a direct converter;

FIG. 2 shows a known digital radiographic unit in accordance with FIG. 1 having an x-ray quantum impinging in limited fashion on a central pixel evaluation unit, and having a threshold value;

FIG. 3 shows a known digital radiographic unit in accordance with FIG. 1 having an x-ray quantum impinging in a fashion distributed on two pixel evaluation units, and having a threshold value;

FIG. 4 shows an inventive digital radiographic unit having a direct converter and having an x-ray quantum, distributed on two pixel evaluation units, and two threshold values;

DETAILED DESCRIPTION OF THE EXAMPLE EMBODIMENTS

Figure 5:
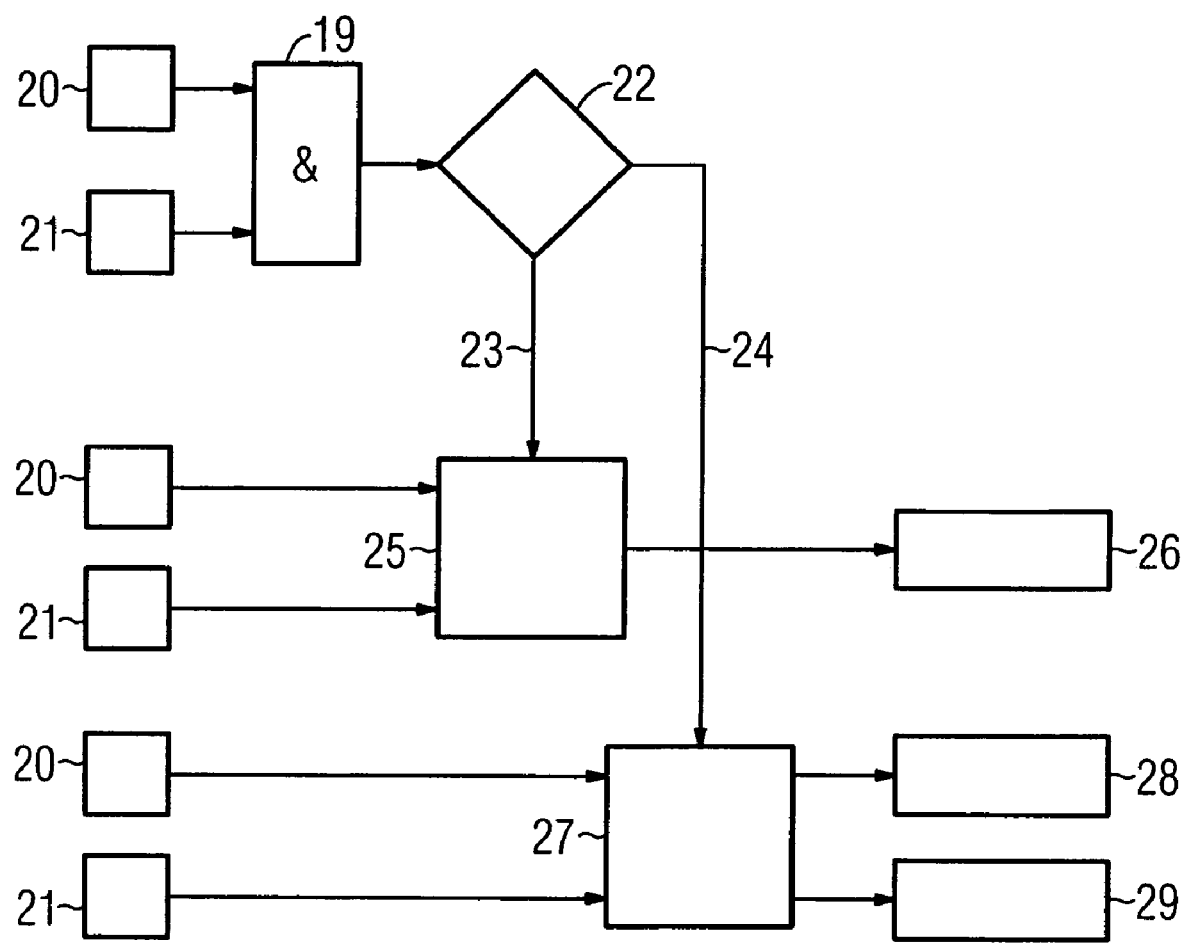
FIG. 5 shows a method sequence for testing a coincidence of the charge pulses of two adjacent pixel evaluation units.

FIG. 1 shows a known, directly converting, counting flat image detector having a direct converter 2. During direct conversion, upon impinging on the direct converter 2 an x-ray quantum 1 of an x-radiation R produces a high-energy electron e that then in turn generates charge carriers 7 on its way through a direct converter 2. The charge carriers 7 are transported with the aid of an electric field to an electrode 4 divided into pixels, and stored there as charges 11. Subsequently, the corresponding charge pulse, which depends first and foremost on the energy of the primary x-ray quantum 1, is read out from a respective pixel readout unit 9 via active switching elements 6 that are electrically linked to one another. The pixel readout unit 9 can be produced as a semiconductor component, for example a CCD chip, APS chip or CMOS chip. At least one embodiment of the invention is equally valid for an indirectly converting flat image detector having a scintillator, and for a directly converting flat image detector having a direct converter 2.

FIG. 2 shows the flat image detector in accordance with FIG. 1, the charge pulse 12 that is generated by the x-ray quantum 1, can be read out from the central pixel readout unit 9 and can be represented, for example in units of energy E, overshooting a lower threshold value S1 defining a background noise. The charge pulse 12 is interpreted in this case as a signal of a single x-ray quantum 1. Shown in FIG. 3 in a fashion distributed on two adjacent pixel readout units 9; 10 are charges 11 that are caused by an x-ray quantum 1 and that generate a first charge pulse 12 in the central pixel readout unit 9 and a second charge pulse 13 in an adjacent pixel readout unit 10. Since the two charge pulses are below the lower threshold value S1, they are neglected and—in the present known case—the x-ray quantum 1 is not counted incorrectly in the evaluation.

FIG. 4 shows a flat image detector according to at least one embodiment of the invention in the case of which a coincidence of the first charge pulse 12 of the central pixel readout unit 9 and the second charge pulse 13 of the adjacent pixel readout unit 10 is detected and the charge pulses 12; 13 are summed to form a total charge pulse 15. Here, the total charge pulse 15 is to be understood as the energy resulting from the individual charge pulses 12; 13. A coincidence circuit can be implemented as described below, for example: a central pixel evaluation unit 9 registers a charge pulse 12 and thereby starts a time counter whose counting time has elapsed after a prescribed time interval. If a charge pulse 13 is registered in an adjacent pixel readout unit 10 within this time interval, the first charge pulse 12 and the second charge pulse 13 are regarded as coinciding.

In the simplest case, upon the occurrence of a coincidence the total charge pulse 15 is assigned to the central pixel evaluation unit 9 as representation of an x-ray quantum 1. However, it is also possible to provide that in addition to the coincidence other, further conditions such as, for example, the overshooting of a lower threshold value S1 defining a noise, or the undershooting of an upper threshold value S2 defining two x-ray quanta are fulfilled. For example, the total charge pulse 15 is evaluated as energy of a single x-ray quantum 1 in the case when it overshoots the lower threshold value S1 defining a background noise, and undershoots the second, upper threshold value S2, and an x-ray quantum 1 is counted with the total charge pulse 15 at the position of the central pixel readout unit 9.

FIG. 5 shows an example of a method sequence of a coincidence circuit as a flowchart. Starting from the output 20 of the central pixel readout unit 9, and from the output 21 of the adjacent pixel readout unit 10, an AND gate 19 checks whether in the case of both one signal, that is to say a charge pulse, each is registered. Upon confirmation, a check is made in a first branch 22 adjacent thereto as to whether the charge pulses of the two pixel readout units have occurred within a previously established time interval, that is to say whether the coincidence condition is fulfilled.

If this condition is fulfilled, a yes output 23 of the first branch 22 passes a message to a first adder 25. There, the sum of the charge pulses, that is to say the total energy, of the central pixel readout unit 9 and the adjacent pixel readout unit 10 is added. The first adder 25 leads to a first counter 26 in which an x-ray quantum having the total charge pulse is counted as total energy for one of the pixel readout units 9; 10.

In an advantageous way, the pixel readout unit 9; 10 that initiates the time interval is provided for measuring and counting the respective first x-ray quantum 1. The x-ray quantum 1 can, for example, be counted for the central pixel readout unit 9.

If the condition is not fulfilled, a no output 24 of the first branch 22 passes a message to a bypass 27, and the charge pulses are processed further in a separate fashion, specifically, one is counted in a second counter 28, and the other in a third counter 29. The charge pulse of the central pixel readout unit 9 is counted in this case by the central pixel readout unit 9 as an x-ray quantum 1 having corresponding energy, and the charge pulse of the adjacent pixel readout unit 10 is counted by the adjacent pixel readout unit 10 as an x-ray quantum 1 with corresponding energy.

Figure 6:
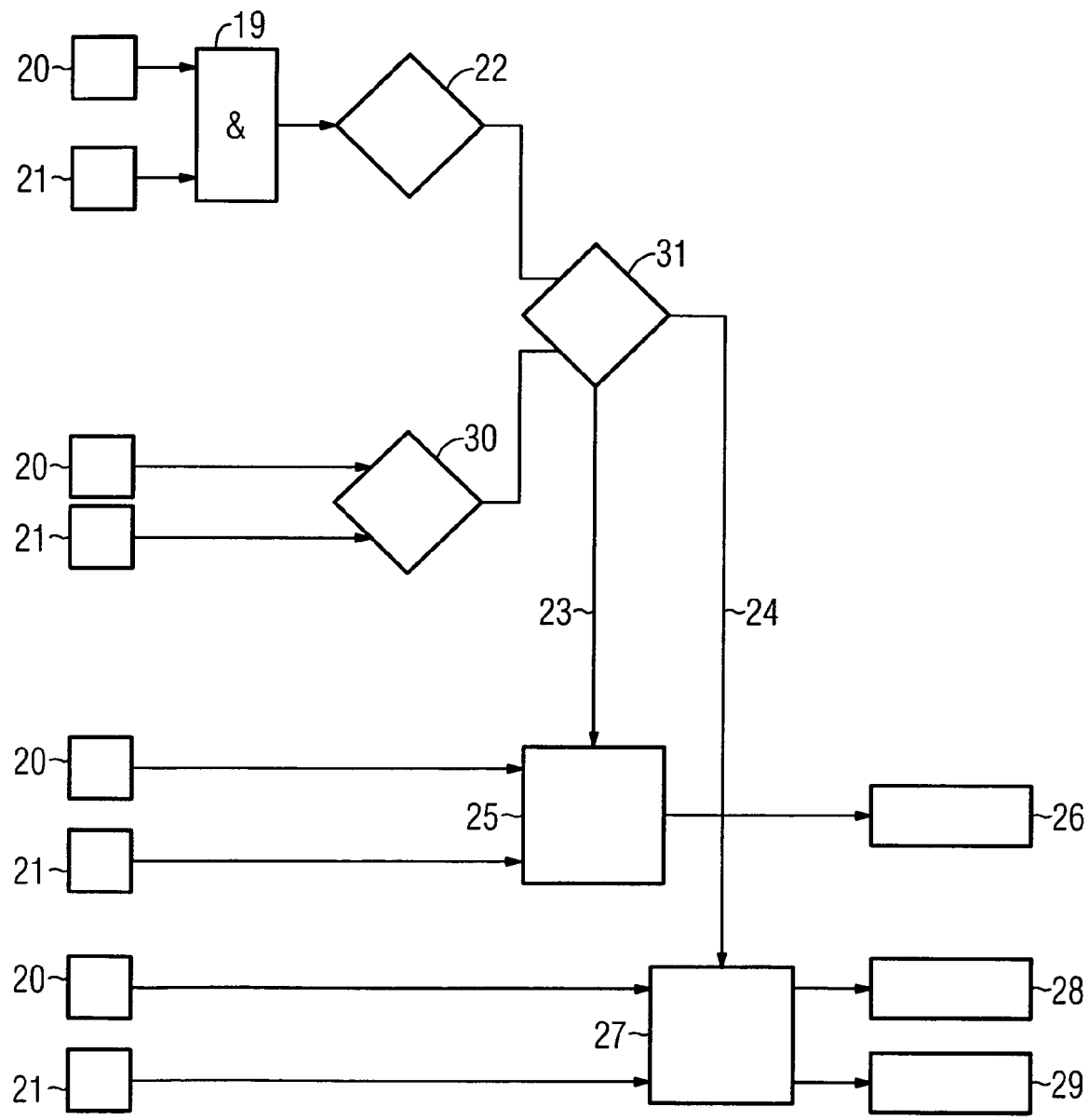
FIG. 6 shows a further method sequence for testing a coincidence with the aid of a threshold value condition of the charge pulses of two adjacent pixel evaluation units.

FIG. 6 shows an example of a method sequence, additionally equipped with a threshold value condition, of a coincidence circuit, as a flowchart. In addition to the checking in the first branch 22 as to whether the coincidence condition is fulfilled, a check is simultaneously made in a second branch 30 as to whether a threshold value condition, for example the overshooting of the lower threshold value defining a background noise, is fulfilled. A check is made in a third branch 31 as to whether both conditions, that is to say coincidence conditions and threshold value condition, are simultaneously fulfilled and then a message is passed on in accordance with the result from the no output 38 or yes output 37 of the third branch 31.

Figure 7:
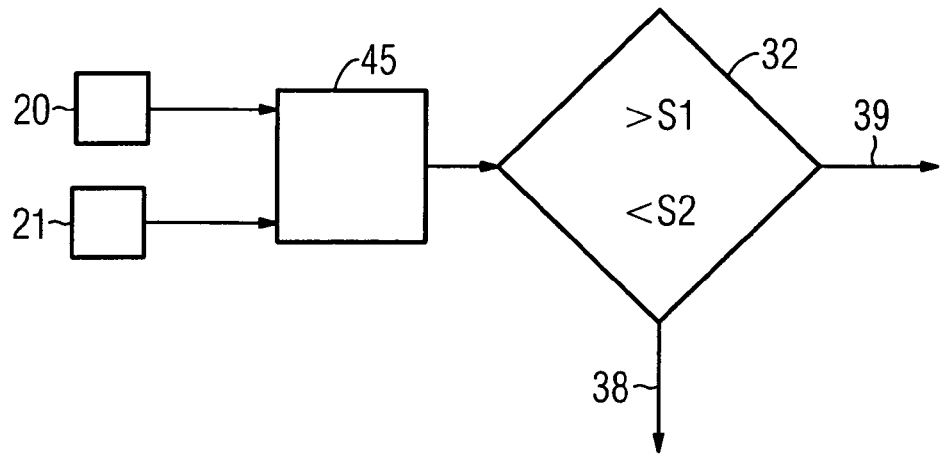
FIG. 7 shows a method for testing a threshold value condition that is alternative to FIG. 6.

FIG. 7 shows an example of a threshold value condition alternative to the second branch 30 in FIG. 6, as a flowchart. The charge pulses of the central pixel readout unit 9 and the adjacent pixel readout unit 10 are summed in a second adder 45, and the total charge pulse 15, that is to say the total energy, is checked thereupon in a fourth branch 32 as to whether it is simultaneously above the lower threshold value S1 defining a background noise and below the upper, defined threshold value S2.

The upper, defined threshold value S2 will preferably be selected such that it is greater than a typical single charge pulse, and smaller than two typical individual charge pulses. If the threshold value condition is fulfilled, a connection is provided via a yes output 43 of the fourth branch 32 to the third branch 31—as already explained in accordance with FIG. 6—while if it is not fulfilled a no output 44 of the fourth branch 32 leads to a truncation of the common consideration of the charge pulses of the central pixel readout unit 9 and the adjacent pixel readout unit 10.

Figure 8:
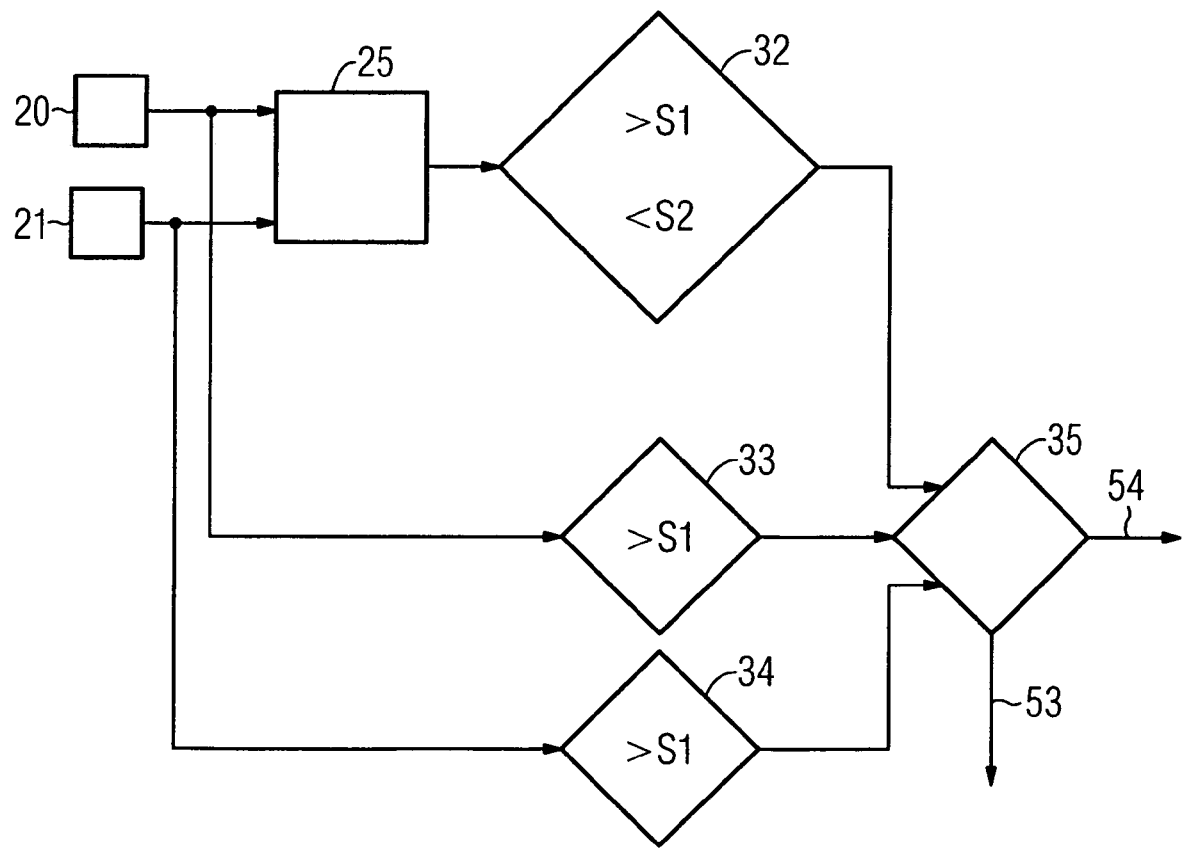
FIG. 8 shows a further method for testing a threshold value condition that is alternative to FIG. 6.

FIG. 8 shows a further example of a threshold value condition alternative to the second branch 30 in FIG. 6, as a flowchart. The charge pulse of the central pixel readout unit 9 is checked thereupon in a fifth branch 33 as to whether it exceeds the lower threshold value S1 defining a background noise; the charge pulse of the adjacent pixel readout unit 10 is likewise checked in a sixth branch 34 for the overshooting of the lower threshold value. At the same time, the total charge pulse 15 summed in a second adder 45 is checked thereupon as to whether it is simultaneously above the lower threshold value S1 and below the upper, defined threshold value S2.

In a seventh branch 35, a check is made as to whether all three threshold value conditions are fulfilled simultaneously. If this is the case, a yes output 53 of the seventh branch 35 leads to the third branch 31 in which a check is made as to whether coincidence condition and threshold value conditions are simultaneously fulfilled, as already explained in accordance with FIG. 6. If one threshold value condition or a number of the three threshold value conditions is/are not fulfilled, a third no output 54 of the seventh branch 35 leads to a truncation of the common consideration of the charge pulses of the central pixel readout unit 9 and the adjacent pixel readout unit 10.

Such method sequences can be applied for each pixel readout unit and their respective adjacent pixel readout units. Here, both a neighborhood adjoining via a lateral edge, and a neighborhood adjoining by a corner are to be considered as adjacent. A rectangular pixel readout unit generally has up to eight adjacent pixel readout units. For differently shaped pixel readout units, for example triangular or octagonal, it is possible in each case to define appropriately adjacent pixel readout units. Similar methods can also be used for more than two adjacent pixel readout units.

At least one embodiment of the invention may be summarized as follows: in order to improve radiographs in the case of a digital radiographic unit having a counting flat image detector for taking radiographs from an x-radiation with the aid of pixel readout units, adjacent in a matrix, for measuring and counting charge pulses generated by x-ray quanta of the x-radiation, it is proposed to provide to detect a coincidence, occurring within a specific time interval, of charge pulses of a pixel readout unit and of charge pulses of at least one bordering pixel readout unit, and to sum the corresponding charge pulses to form a total charge pulse as basic variables for a further evaluation.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for taking radiographs in a digital radiographic unit, wherein with the aid of pixel readout units adjacent in a matrix, charge pulses generated by x-ray quanta are measured and counted by using a counting flat image detector, that the method comprising:
measuring a coincidence, occurring within a specifiable time interval, of a charge pulse of a matrix readout unit and a charge pulse of at least one bordering matrix readout unit;
adding the corresponding charge pulses to form a total charge pulse; and
providing coincidence measurement and total charge pulse as basic variables for a further evaluation;
reading out, for a given coincidence, a number of x-ray quantum as image information for a radiograph, the number of x-ray quantum being zero, one x-ray quantum or two x-ray quantum depending on a height of the total charge pulse relative to a lower and upper threshold value; and
generating radiographs based on the image information and taking into account results of the further evaluation; wherein
the time interval is functionally dependent in terms of initiation on a pixel readout unit that records a first charge pulse.

2. The method as claimed in claim 1, wherein given a coincidence, an x-ray quantum is read out and is provided with an energy corresponding to the total charge pulse as image information for a radiograph.

3. The method as claimed in claim 2, wherein given a coincidence, and when the total charge pulse undershoots a lower threshold value defining a background noise, no x-ray quantum is read out and provided as image information for a radiograph.

4. The method as claimed in claim 3, wherein given a coincidence, and when the total charge pulse overshoots an upper defined threshold value, two x-ray quanta are read out and provided as image information for a radiograph.

5. The method as claimed in claim 2, wherein given a coincidence, and when the total charge pulse overshoots an upper defined threshold value, two x-ray quanta are read out and provided as image information for a radiograph.

6. A method for taking radiographs in a digital radiographic unit, wherein with the aid of pixel readout units adjacent in a matrix, charge pulses generated by x-ray quanta are measured and counted by using a counting flat image detector, that the method comprising:
measuring a coincidence, occurring within a specifiable time interval, of a charge pulse of a matrix readout unit and a charge pulse of at least one bordering matrix readout unit;
adding the corresponding charge pulses to form a total charge pulse;
providing coincidence measurement and total charge pulse as basic variables for a further evaluation;
reading out, for a given coincidence, a number of x-ray quantum as image information for a radiograph, the number of x-ray quantum being zero, one x-ray quantum or two x-ray quantum depending on a height of the total charge pulse relative to a lower and upper threshold value; and
generating radiographs based on the image information and taking into account results of the further evaluation; wherein the time interval is initiated by a pixel readout unit that records a first charge pulse.

7. The method as claimed in claim 6, wherein a respective first x-ray quantum is measured and counted by the pixel readout unit initiating the time interval.

8. The method as claimed in claim 6, wherein the pixel readout unit is a central pixel readout unit.

9. A method for taking radiographs in a digital radiographic unit, the method comprising:
measuring a coincidence, occurring within a specifiable time interval, of a charge pulse of a matrix readout unit and a charge pulse of at least one bordering matrix readout unit;
adding the corresponding charge pulses to form a total charge pulse, coincidence measurement and total charge pulse being usable as basic variables for a further evaluation;
reading out, for a given coincidence, a number of x-ray quantum as image information for a radiograph, the number of x-ray quantum being zero, one x-ray quantum or two x-ray quantum depending on a height of the total charge pulse relative to a lower and upper threshold value; and generating radiographs taking into account results of the further evaluation; wherein the specifiable time interval is functionally dependent in terms of initiation on a pixel readout unit that records a first charge pulse.

10. The method as claimed in claim 9, wherein given a coincidence, an x-ray quantum is read out and is provided with an energy corresponding to the total charge pulse as image information for a radiograph.

11. The method as claimed in claim 10, wherein given a coincidence, and when the total charge pulse undershoots a lower threshold value defining a background noise, no x-ray quantum is read out and provided as image information for a radiograph.

* * * * *